US005905196A

United States Patent [19]

Parshall

[11] Patent Number: 5,905,196

[45] Date of Patent: May 18, 1999

[54] ROTATIONAL VISCOMETER TEMPERATURE SENSOR

[75] Inventor: Thomas K Parshall, Hartland, Mich.

[73] Assignee: Kaltec Scientific, Inc., Novi, Mich.

[21] Appl. No.: 09/003,957

[22] Filed: Jan. 7, 1998

[51] Int. Cl.[6] .............................. G01N 11/14; G01J 05/12

[52] U.S. Cl. ........................ 73/54.31; 73/54.02; 73/54.42; 374/130; 356/427

[58] Field of Search ................................ 73/54.31, 54.32, 73/54.02, 54.42, 54.43, 54.24; 374/130; 556/51; 356/427

[56] References Cited

U.S. PATENT DOCUMENTS

| | | | |
|---|---|---|---|
| 2,076,816 | 4/1937 | Hess | 265/11 |
| 2,598,178 | 5/1952 | Källe | 73/357 |
| 2,603,087 | 7/1952 | Hortenau | 73/59 |
| 3,056,283 | 10/1962 | Tiede | 73/59 |
| 3,111,838 | 11/1963 | Bucalo | 73/54 |
| 3,225,191 | 12/1965 | Calhoun | 250/43.5 |
| 3,382,706 | 5/1968 | Fitzgerald et al. | 73/59 |
| 3,568,693 | 3/1971 | Vandrey | 137/1 |
| 3,803,384 | 4/1974 | Braunlich | 250/345 |
| 4,077,252 | 3/1978 | Stutz et al. | 73/59 |
| 4,800,279 | 1/1989 | Hieftje | 250/339 |
| 4,878,379 | 11/1989 | Deer | 73/60 |
| 5,271,675 | 12/1993 | Fagan et al. | 374/110 |
| 5,317,908 | 6/1994 | Fitzgerald et al. | 73/54.26 |
| 5,339,255 | 8/1994 | Suzuki et al. | 364/500 |
| 5,348,396 | 9/1994 | O'Rourke et al. | 374/161 |
| 5,399,018 | 3/1995 | Hollander et al. | 374/121 |
| 5,445,035 | 8/1995 | Delajoud | 73/861.52 |
| 5,540,088 | 7/1996 | Hall | 73/54.43 |

*Primary Examiner*—Hezron E. Williams
*Assistant Examiner*—J. David Wiggins
*Attorney, Agent, or Firm*—Young & Basile, P.C.

[57] ABSTRACT

A viscometer has a rotatable member and a stationary wall engageable with material to be measured. A lens extends through at least a portion of the wall of the viscometer such that laminar flow of material to be measured is undisturbed while shearing across a face of the lens. An infra-red sensor is alignable through the lens for directly measuring infra-red energy created while the material shears across the face of the lens in response to the rotatable member moving with respect to the lens. A method is disclosed for measuring a torque of a material to be tested in a viscometer has a rotatable member and a wall engageable with material to be measured. The method includes the step of shearing material to be measured during undisturbed laminar flow across a face of a lens extending through at least a portion of the wall of the viscometer, and sensing infra-red energy with an infra-red sensor alignable through the lens for directly measuring infra-red energy created while the material to be measured shears across the face of the lens in response to the rotatable member moving with respect to the lens and wall.

20 Claims, 7 Drawing Sheets

28 26 20 36 10 32 22 24 18 34 30 TEMPERATURE SENSOR 12 40 38 42 INPUT DEVICE COMPUTER OR MICRO-PROCESSOR OUTPUT DEVICE

ROTATIONAL VISCOMETER TEMPERATURE SENSOR

FIELD OF THE INVENTION

The present invention relates to a method and apparatus for measuring temperature, or other physical characteristics, of a solid or fluid while in motion and inaccessible, and more particularly to a method and apparatus for measuring the infra-red energy created as the material to be measured is shearing across a face of an infra-red transparent lens.

BACKGROUND OF THE INVENTION

Infra-red sensor devices are widely used for sensing and measuring temperature conditions in various industrial and scientific environments. The sensor elements are typically sold as a unit encapsulated in a cylindrical outer case to protect the sensor elements which are usually small, fragile and generally difficult to handle. The case provides physical and mechanical protection for the sensor elements. A sensing face of the infra-red sensor is typically located at one axially end of the cylindrical case, and electrical conductor leads capable of being attached to internal circuitry of the sensor extend from a position typically at or near the opposite end of the cylindrical outer case.

It is known to mount infra-red sensors in fixed locations relative to a test surface or area having a temperature characteristic to be monitored. Mounting typically is accomplished by a bracket having various gripping or clamping devices of well-known design. The bracket or other support is capable of being attached to any suitable, appropriately located surface, such as a fixed portion of a related apparatus, or other structure in which the sensor or related apparatus is enclosed. The sensing face of the sensor is aimed at a desired portion of a surface to be monitored. Generally, the distance between the sensing face and the monitored test surface is selected to control the total amount of surface area that falls within the operable range of the sensor. Accurate positioning relative to the surface to be monitored is required in order to obtain accuracy, reliability and overall usefulness of the sensor signals. The sensor signals are directly dependent on precise determination of the distance between the sensor face and the surface to be monitored. If the distance is greater than intended or less than intended, erroneous temperature readings are likely to result, or the sensor may fail to monitor the proper area of the surface to be monitored.

Known optical temperature measurement devices include a probe having a sensor with temperature-dependent light-absorbing properties. The sensor is in optical communication with a source of light and a detector such as a spectrophotometer. A characteristic factor and a temperature-dependent factor can be derived from measurements of the amount of light transmitted through the sensor by analyzing the change in the absorbance characteristics of the sensor material with changes in temperature. The choice of temperature-sensing materials depends on the desired temperature range and sensitivity of the measurement, and the physical condition expected at the location. The sensor can be made of substantially non-electrically-conducting materials to minimize electrical interference when used in electromagnetic fields and near sources of leakage current. The probe can be made of substantially non-electrically-conducting and non-thermally-conducting materials, minimizing the effects of stray electromagnetic fields, leakage currents, and thermal conductivity on the measurement. Additional information regarding known optical temperature measurement devices and methods can be obtained from U.S. Pat. No. 5,358,396 issued on Sep. 20, 1994 which is incorporated herein by reference. Additional details regarding infra-red thermal couples can be obtained from U.S. Pat. No. 5,399,018 issued Mar. 21, 1995 which is incorporated herein by reference.

SUMMARY OF THE INVENTION

The present invention relates to a method and apparatus of measuring temperature or other physical characteristic of a solid or fluid while the solid or fluid is in motion, or otherwise inaccessible. The present invention involves placing a window or lens at the point of measurement so that the characteristics of the solid or fluid can be determined while in motion. The lens can be optically clear, or transparent to other means of measurement by devices such as an infra-red sensor, optical spectrometer, or the like. The lens is designed to avoid creating any turbulence in the fluid, or friction in the solids. The lens can be any size, depending on the circumstances of the material to be tested. The combination of a lens and infra-red sensor provides a non-contact temperature measurement, thereby eliminating the problems associated with having thermocouple wiring connected to the cup which would cause problems with the torque measurements being taken.

In a rotational viscometer of the cup and bob type, with a rotating bob, the lens is bonded into the side of the cup with a smooth, seamless surface on the inside diameter of the cup so as not to disturb the laminar flow of the material being tested. The material is sheared on the cup wall and across the face of the lens. The result is that the present invention measures the infra-red energy created by the shearing directly, as opposed to indirectly with other techniques. In a cone and plate viscometer, the lens would be placed in the plate. Placing a quartz lens in the cup would permit spectrographic analysis of a sample. The lens used for infra-red measurement is manufactured by Amorphous Materials, Inc. of Garland, Tex. from an AMTIR-1 material which has a transmittance of about 1.4 microns and zero attenuation at that wave length.

The thermal sensor according to the present invention is an infra-red probe that senses through a window in the cup to measure the temperature at a rate of approximately every 60 milliseconds. A temperature graph can be plotted and can be compared to changes in rheological properties of liquids. Typically, standard viscosity oil is used to calibrate viscometers, however this calibration method is subject to inaccuracies due to the temperature dependency of standard viscosity oil. The infra-red sensor, by providing temperature data, assists in accurately calibrating the viscometer when using a known viscosity standard. A high shear viscometer system according to the present invention combines a very sensitive torque sensor under computer control to produce results of greater precision with a high level of reproducibility. Computer control removes any operator influence from the results produced by the system. High shear viscometer systems can be used for quality control, and diagnostics to predict performance of coatings during the application process. The present invention provides a quick, precise, versatile, reproducible, durable and operator friendly viscometer system capable of measuring shear rate of liquids and temperature during testing procedures. The viscometer measures torque (an independent variable) in the presence of an increasing and decreasing shear rate (a dependent variable). Torque values are then used to calculate viscosity and/or-shear stress.

The present invention includes a viscometer for measuring shear rate of a liquid, or solids suspended within a liquid.

The viscometer includes a base having a sensitive torque sensor. A container or cup is provided for holding the liquid or material to be tested. The cup or container is engageable with the base. The container has at least one side wall with at least a portion of the side wall defining a window or lens of substantially optically-transparent material with temperature-dependent optical transmission characteristics within a characteristic wave length range.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
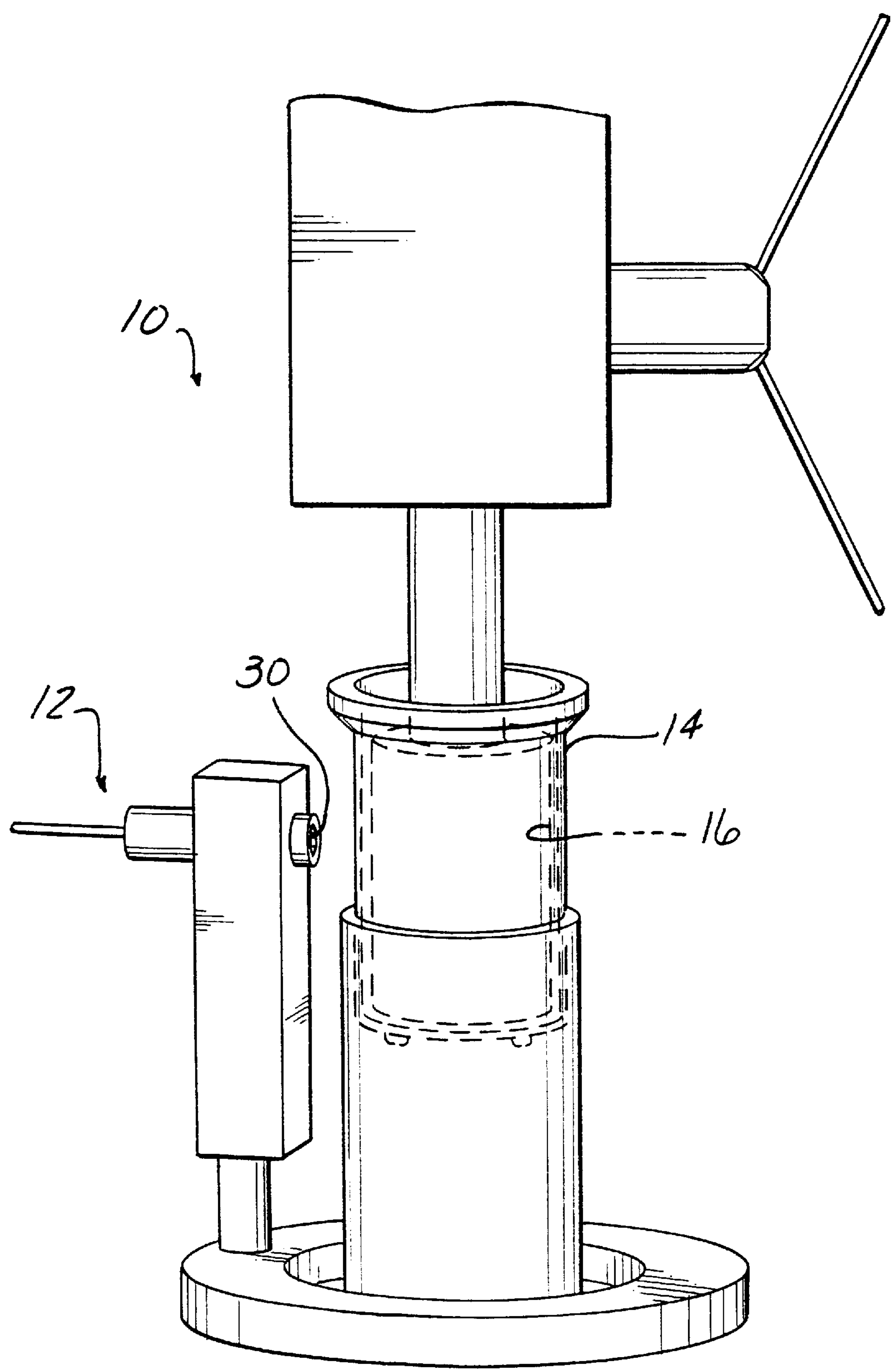
FIG. 1 is a perspective view of a cup and bob type rotational viscometer according to the present invention.
Figure 2:
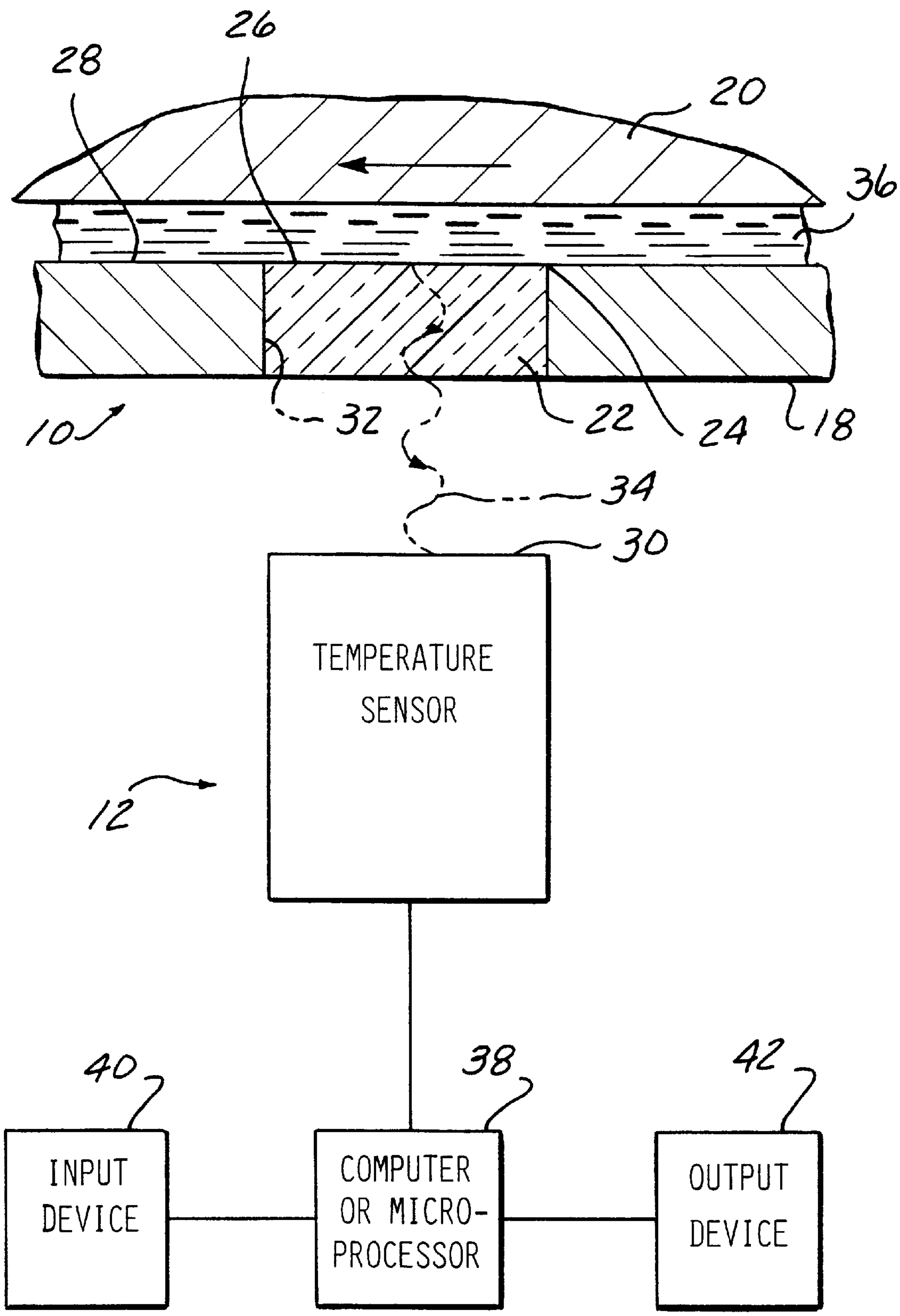
FIG. 2 is a schematic view of an infra-red sensor for measuring the temperature of a fluid shearing across a face of a transparent lens or window supported in a wall containing the fluid.

FIG. 1 illustrates a typical known rotational viscometer 10 having the improvement of a temperature sensor 12 according to the present invention. The previously known rotational viscometer 10 can include a cup 14 and bob 16 as illustrated in FIG. 1, or a wall or plate 18 and cone 20 as illustrated in FIG. 2. In either case, the viscometer 10 according to the present invention provides a lens 22 passing through the wall of the cup 14 or plate 18 with a smooth seamless edge 24 between a face 26 of the lens 22 and a surface 28 of the wall, such that laminar flow of material to be measured is undisturbed while shearing along the surface 28 of the wall and across the face 26 of the lens 22. An infra-red sensor 30 is positionable spaced from the wall and alignable with the lens 22 for sensing through the lens 22 for directly measuring infra-red energy created while the material shears across the face 26 of the lens 22. The movement of the material across the face 26 of the lens 22 can be in response to any fluid flow motivator. By way of example and not limitation, the fluid flow motivator in a rotational viscometer as illustrated in FIG. 1 is a bob 16, or as illustrated in FIG. 2 is a cone 20. The fluid flow motivator can also include mechanical devices or natural forces for creating static or dynamic forces resulting in shearing fluid flow across the face of the lens 22. The lens 22 can form the entire wall of the vessel, container, conduit, passage, or the like, allowing measurement of the temperature of the shearing fluid flow at any location along the wall, or preferably formed of at least a portion of the wall of the vessel, container, conduit, passage, or the like. The present invention provides a window or lens 22 at the point of measurement so that characteristics of the fluid or suspended solid can be determined while in motion. The lens 22 can be optically clear, or transparent to other means of measurement by devices such as an infra-red sensor, optical spectrometer, or the like. The lens 22 is contoured to the surface of the container, vessel, conduit, passage, or the like to avoid creating any turbulence in the fluid, or friction in the suspended solids. The lens can be any size.

In the preferred configuration of a rotational viscometer of the cup and bob type with a rotating bob 16, the lens 22 is bonded into the wall of the cup 14 with a smooth, seamless surface on the inside diameter of the cup 14 so as to not disrupt the laminar flow of the material being tested. Therefore, the material is sheared on the wall of the cup 14 and across the face 26 of the lens 22. The results is the measurement of the infra-red energy created by the shearing directly, as opposed to indirectly with all other previously known techniques. In a cone and plate viscometer, the lens 22 can be placed in the wall of the plate 18. Selecting a quartz lens for placement in the wall would permit spectrographic analysis of a sample. Preferably, the lens 22 used for infra-red measurement is manufactured from AMTIR-1 material, which has a transmittance of about 1.4 microns and zero attenuations at that wavelength. The lens material is manufactured by Amorphous Materials Inc. of Garland, Tex. The infra-red probe senses through the lens 22 in the cup 14 to measure the temperature at a predetermined rate, preferably every 60 milliseconds. A temperature graph can be plotted and compared to changes in shear rate of the fluid.

The lens material can be bonded in place using an epoxy adhesive called OMEGA BOND® 101 from Omega Engineering Inc. of Stanford, Conn., which is a commercially available two part epoxy resin. The epoxy resin forms an adhesive layer 32 to join the lens 22 to the wall contacting the material to be measured. The lens 22 can be made of ceramic, quartz, or other suitable material transparent to at least infra-red wavelengths. The wall of the cup 14 or plate 18 contacting the material to be measure can be constructed of ceramic, effectively making the entire wall a lens, or other suitable material different from the lens material, such as stainless steel, or the like. It is anticipated that the face 26 of the lens 22 could be treated with other materials such as boron or the like, to increase accuracy of the temperature measurement.

Figure 3:
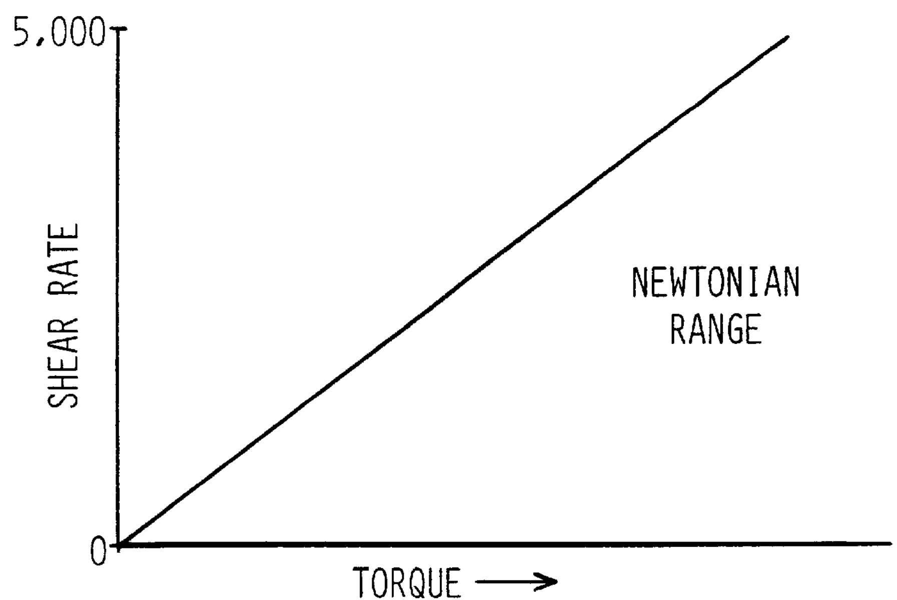
FIG. 3 is an illustrative graph depicting shear rate in reciprocal seconds ($sec^{-1}$) versus torque for a fluid in a newtonian range.
Figure 4:
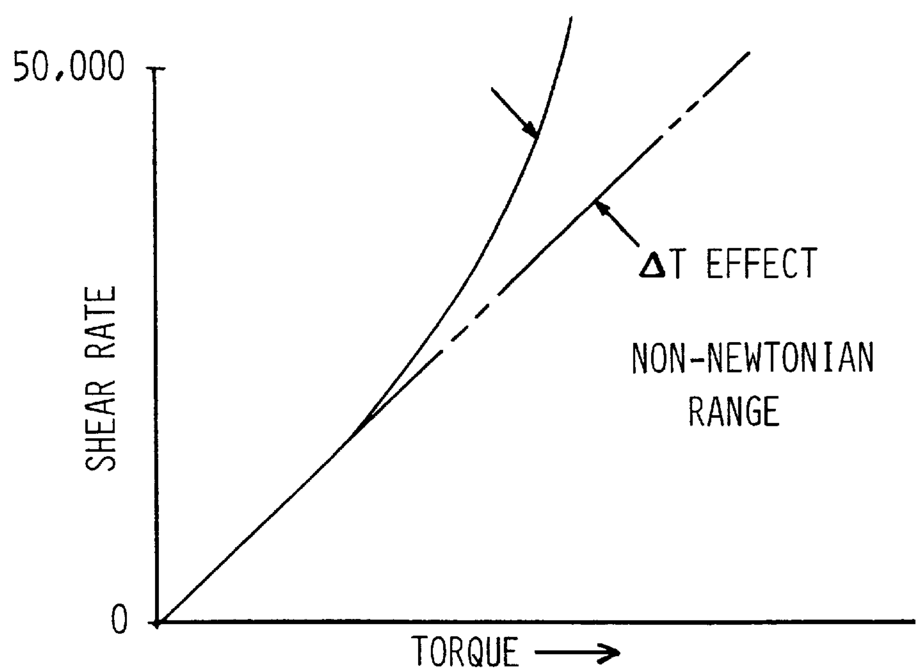
FIG. 4 is an illustrative graph showing shear rate versus torque for a fluid in a non-newtonian range showing the effect of temperature change on the fluid.

In operation, a rotational viscometer of the cup and bob type typically operates between 0 to 8,800 revolutions per minute over a time span of approximately 20 seconds to minimize any increase in temperature of the material to be measured. The best temperature measurement available from the prior art devices was with use with a viscometer of the cone and plate type, which is not usable with high shear or "sloppy" materials. Typically, the temperature variation of the material to be tested during the testing procedure can vary from a minimum change in temperature of 0° C. (Celsius) to a maximum change in temperature of approximately 30° C. (Celsius). As illustrated in FIGS. 3 and 4 of the present application, the differences in shear rate versus torque for a newtonian fluid and non-newtonian fluid is depicted. Essentially, a newtonian fluid has no change in torque for the temperature rise produced during the testing procedure of shear rates below 5000 second$^{-1}$, while the same fluid demonstrates a change in torque as the temperature rises during the testing procedure of shear rates above 5000 second$^{-1}$. The graphs of FIGS. 3 and 4 illustrate the concept of the possible changes in torque as a result of temperature rises, and are not meant to illustrate any particular material or testing procedure performed with the present invention. The actual graphic results of tests performed using an apparatus according to the present invention can vary from that depicted depending on the material being tested and its specific sensitivity to temperature rises during the testing procedure.

As illustrated in FIG. 2, the present invention includes a temperature sensor 12 for sensing infra-red energy 34 generated by the fluid 36 shearing across the face 26 of the lens 22. The temperature sensor 12 generates a signal corresponding to the sensed infra-red energy 34. The signal generated by the temperature sensor 12 is communicated to a central processing unit, microprocessor, or computer 38. The central processing unit, microprocessor, or computer 38 can receive additional input signals from other input devices 40, by way of example and not limitation, such as keyboards, spectrometers, or the like. In addition, the central processing unit, microprocessor, or computer 38 can generate signals for delivery to output devices 42, by way of example and not limitation, such as a display monitor, a printer, a storage device, a serial port, a modem, or the like.

Figure 5:
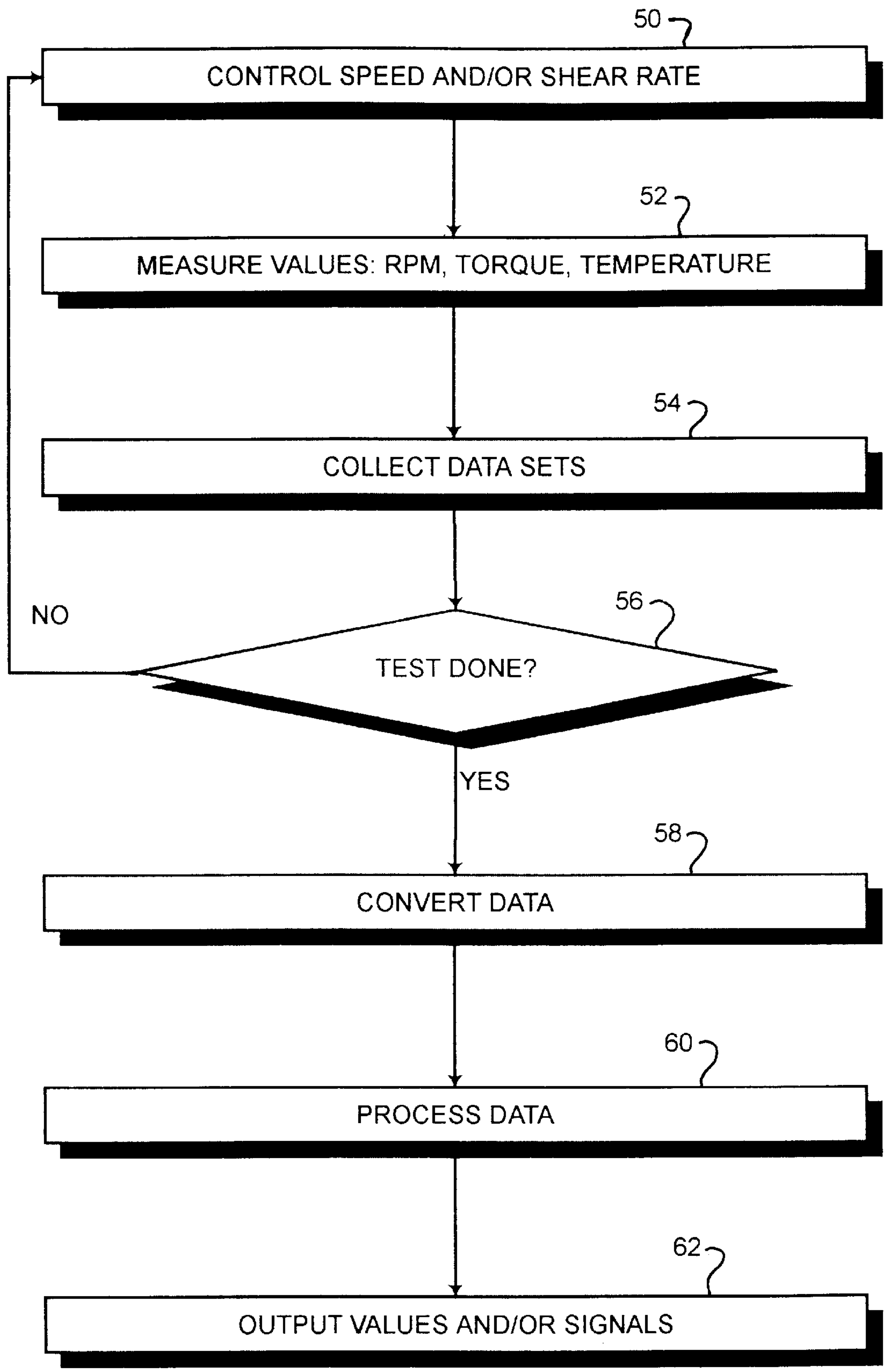
FIG. 5 is a flow diagram illustrating an overall process according to the present invention.

FIG. 5 is a flow diagram illustrating the overall process of the testing procedure according to the present invention. Referring now to FIG. 5, the speed of the bob 16 or cone 20 is controlled in step 50 by the central processing unit, microprocessor, or computer 38. Values are measured in step 52 for operating characteristics, by way of example and not limitation, such as revolutions per minute (rpm), torque, temperature, or the like. The measured values are collected into data sets at predetermined time intervals in step 54. In step 56, the control program inquires whether the test is completed. If the answer to the query in step 56 is no, the program branches back to the control of the speed and/or the shear rate in step 50. If the answer to the query in step 56 is yes, the control program branches to the data conversion step 58. After completion of data conversion in step 58, the control program, continues to the processing of data in step 60. Completion of the data processing in step 60 is followed by generating output signals and/or values as required by the control program in step 62.

Figure 6:
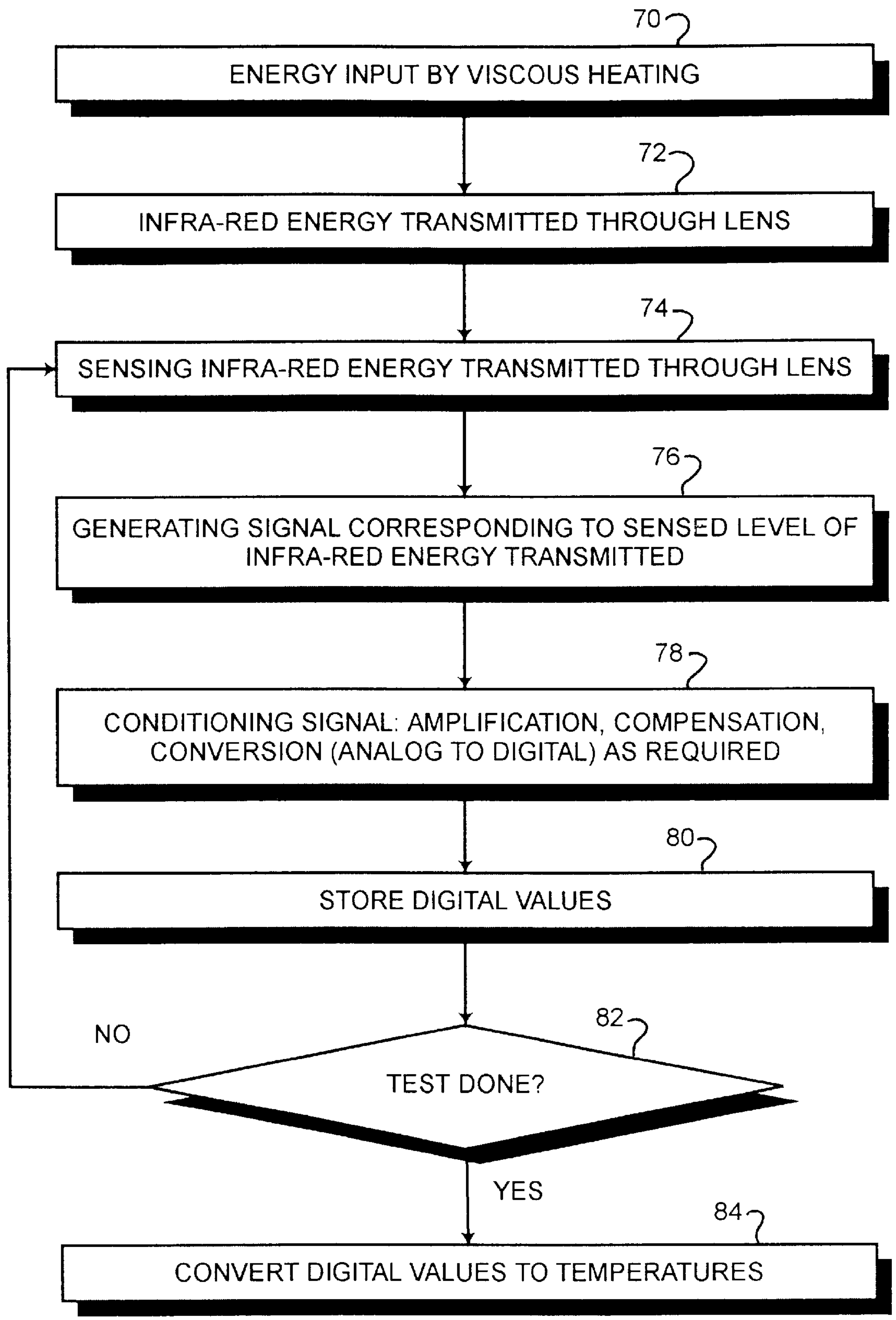
FIG. 6 is a flow diagram illustrating a method of temperature data collection according to the present invention.

Referring now to FIG. 6, specific details of the data collection of temperature values according to the present invention is illustrated in a flow diagram. In step 70, infra-red energy is generated through viscous heating creating the infra-red energy input 34 to the infra-red sensor 30. Infra-red transmission occurs from the heat generation source of viscous heating along the face 26 of the lens 22 through the lens 22 as depicted in FIG. 2 and described in step 72. The infra-red energy 34 is sensed by the infra-red sensor 30 as the infra-red energy 34 is transmitted through the lens 22 in step 74. The temperature data collection process then proceeds to step 76 where the temperature sensor 12 generates a signal corresponding to the sensed level of infra-red energy 34 transmitted through the lens 22. If required, signal conditioning can take place in step 78 including amplification, compensation and/or conversion of the signal from analog to digital, or the like. Digital values are stored in step 80 during the temperature data collection process. After storing the digital value, the data collection process generates a query to determine if the test is complete. If the answer to the query is no, the program branches back to the step 74 for continued sensing of infra-red energy 34 transmitted through the lens 22. If the answer to the query in step 82 is yes, the temperature data collection process continues to step 84 where the stored digital values are converted into actual temperatures.

Figure 7:
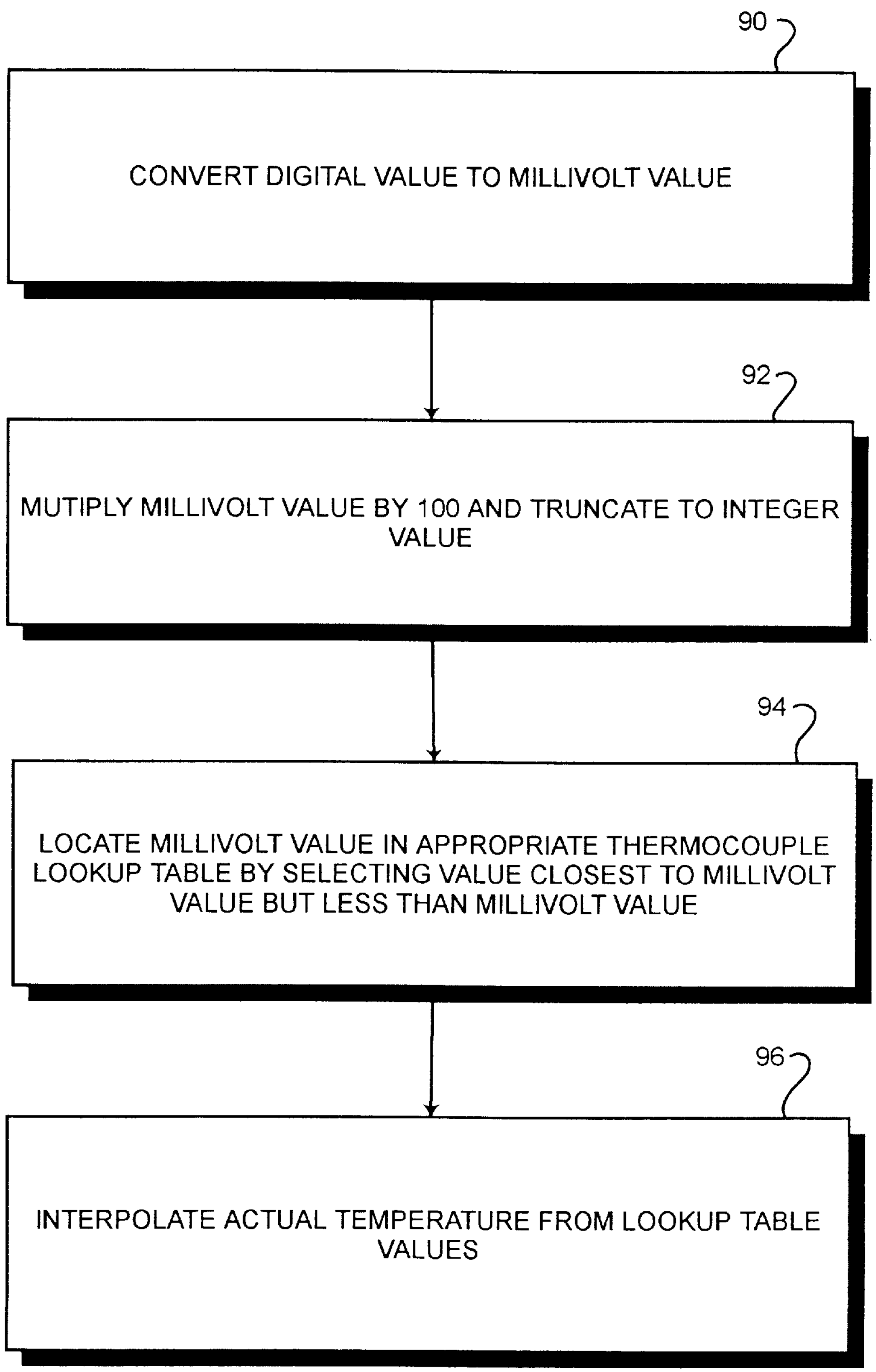
FIG. 7 is a flow diagram illustrating a method of temperature data conversion according to the present invention.

Referring now to FIG. 7, the process of data conversion of temperature values is described in greater detail. In step 90, the program converts a digital value to a millivolt value ($V_s$) by multiplying the digital value by a predetermined constant specific to the infra-red sensor 30. The predetermined constant is set by the manufacturer of the infra-red sensor. The program then continues to step 92 where the millivolt value ($V_s$) is multiplied by 100 and truncated to an integer value. This step is applied in order to increase efficiency of the processing speed without sacrificing accuracy. After the processing of step 92, the millivolt value ($V_s$) is located in an appropriate thermocouple lookup table by selecting the value closes to the millivolt value ($V_s$) but less than the millivolt value ($V_s$) in step 94. The actual temperature value is than determined in step 96 by interpolating the actual temperature from the adjacent lookup table value according to the following formula $$T = T_b + \Delta T_t \frac{(V_s - V_b)}{(V_n - V_b)}$$

where T is the actual temperature, $T_b$ is the base temperature calculated in step 94 and $\Delta T_t$ is the change in temperature between the base millivolt value $V_b$ in the table and the next higher millivolt value $V_n$ in the lookup table, $V_s$ is the millivolt value calculated in step 92, $V_b$ is the base millivolt value found in the lookup step 94 and $V_n$ is the next highest millivolt value in the table after the base millivolt value $V_b$ selected in step 94. This process is repeated for each temperature data value stored during the testing procedure. Preferably, the infra-red sensor 30 of the present invention provides dual temperature value signals providing for two complete data sets simultaneously stored and comparable with respect to one another. The program may also provide for the selection of one or the other data set, or the average of the values collected in the two data sets when processing the data in order to generate output signals and values.

In conclusion, a high-shear viscometer according to the present invention is capable of providing two channels of temperature data. The viscometer contains a thermocouple which is connected to an amplifier and an analog to digital conversion circuit. The output of this temperature circuitry is a digital value representing the number of millivolts being output by the thermocouple. The temperature circuitry is calibrated during manufacture to produce a known number of counts per millivolt which will be used by the software during the conversion process. When the software is being used to run a viscosity test, it also collects both channels of temperature information. Due to the real-time requirements on the software, and the amount of processor time required to convert the digital counts to actual temperatures, only the digital counts are stored during the actual test. Once the test is complete, the data is converted. Immediately following the completion of the viscosity test, the software will convert the digital values stored from both channels of the high-shear viscometer into actual temperature values. The first phase of the conversion is to convert the digital value output from the viscometer into millivolts. This is done using the number of counts per millivolt as set during the viscometer's calibration process. The millivolt value is multiplied by 100 and truncated into an integer value. For speed of processing, all millivolt and temperature data, which may contain fractional components, is stored as a scaled (by 100) integer value rather than a floating point value providing resolution of one hundredth (1/100) of a unit. Once the digital value has been converted into a millivolt value, the second phase of the conversion can take place. Thermocouples output a known number of millivolts for a given applied temperature. These known values are published in tables, which are made public through various avenues. Using the correct thermocouple table, the software locates the millivolt value in the table which is closest to but less than, the millivolt value being converted. The located millivolt value corresponds to an actual temperature as given by the row and column in the table at which the value was found. This temperature will form the base temperature $T_b$ for the value being converted. Each column in the thermal couple conversion table represents a discreet temperature increment. It is unlikely that a millivolt value will correspond exactly to a column in the table. In most cases, it is necessary to interpolate the actual temperature between the base temperature $T_b$ already located, and the temperature $T_n$ given by the next highest temperature increment in the table. The software does this in the final phase of the conversion. To do this, the software uses the ratio between the millivolt value being converted, the millivolt value corresponding to the base temperature, and the millivolt value corresponding to the next greater temperature increment in the table. This value is than multiplied by the temperature increment between values for the table being used ($\Delta T=T_n-T_b$). The fraction of the temperature increment is than added to the base temperature $T_b$ to arrive at the final temperature value T. After a viscosity test has been run and the conversion process has been completed, the resulting data set will consist of the viscosity information and two channels of temperature information which are stored as degrees celsius, scaled by 100, and converted to an integer value for size of storage and speed of manipulation. The software allows the operator to specify which temperature data is to be used during analysis. The choices are either single channel, or an average of the two channels for each point. Because both channels of temperature data are converted and stored, the analysis choice requested by the operator can be easily supplied by the stored data.

Figure 8:
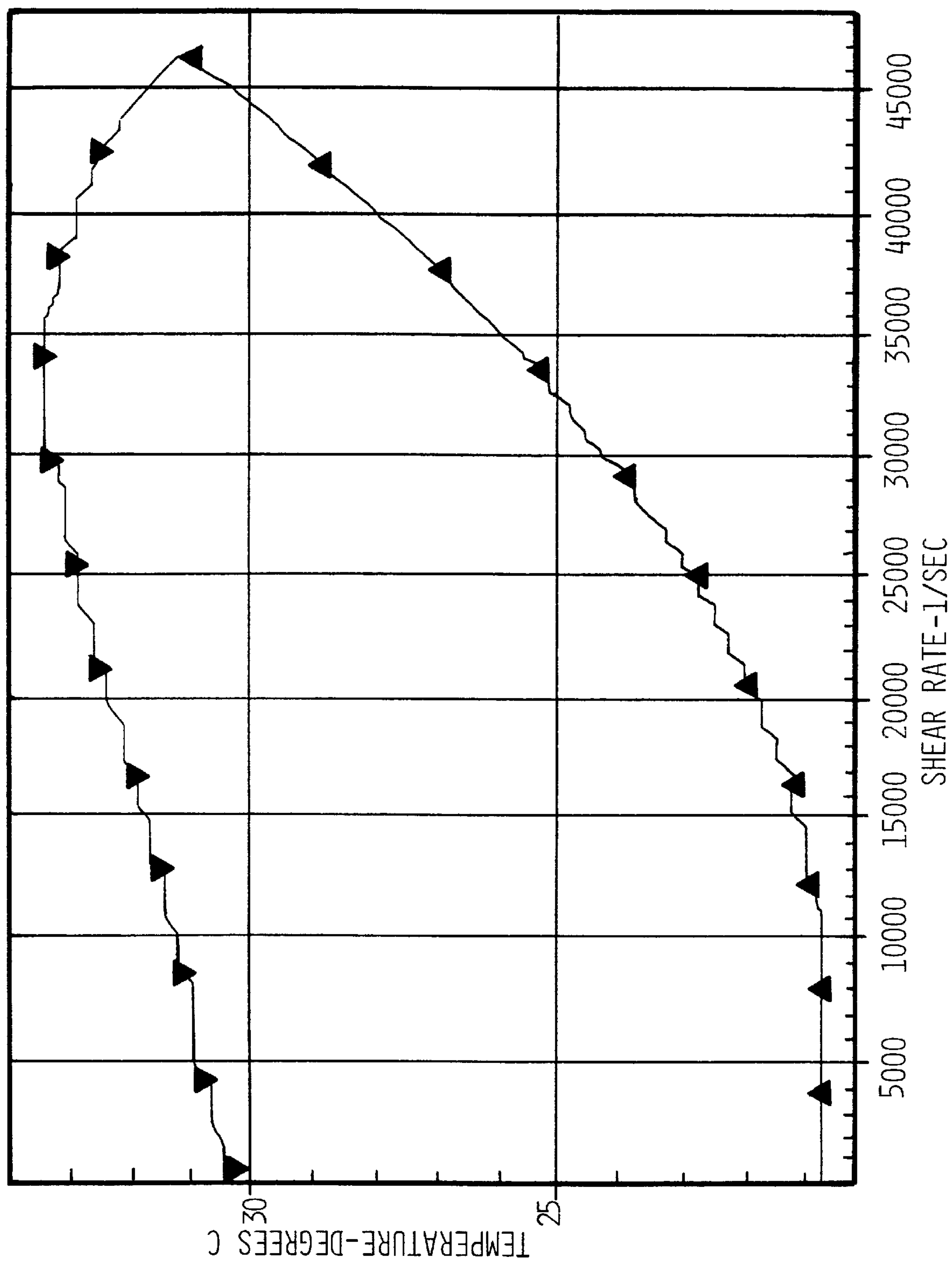
FIG. 8 is an illustrative graph showing temperature versus shear rate for a fluid.

FIG. 8 is an illustrative graph of temperature in degrees Celsius versus shear rate in reciprocal seconds (1/sec). The graph illustrates a test fluid, such as Dow Corning 200 manufactured by Dow Corning in Midland, Mich. The test was conducted using an "E" bob with a maximum speed of 4400 revolutions per minute. The temperature data was collected while driving the "E" bob from 0 to 4400 rpm and returning to 0 rpm over a predetermined time frame. This graph is for illustrative purposes only to show the temperature and shear rate characteristics of a fluid as measured by the present invention. Other fluids may provide graphs of differing characteristics from that illustrated.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. In a viscometer having a rotatable member and a substantially stationary wall engageable with material to be measured, the improvement comprising:

a lens extendible through at least a portion of the wall of the viscometer such that laminar flow of material to be measured is undisturbed while shearing across a face of the lens during rotation of the rotatable member; and an infra-red sensor alignable for sensing through the lens for directly measuring infra-red energy created while the material shears across the face of the lens in response to the rotatable member moving with respect to the lens and substantially stationary wall.

2. The improvement of claim 1 further comprising:

the lens having a smooth seamless edge between the face of the lens and a surface of the wall, the material shearing along the surface of the wall and across the face of the lens undisturbed by the smooth seamless edge.

3. The improvement of claim 1 further comprising:

the sensor positionable spaced from the wall.

4. The improvement of claim 1 further comprising:

the lens formed from an optically transparent material.

5. The improvement of claim 1 further comprising:

the lens having a boron coating applied to the face engageable with the material to be measured.

6. The improvement of claim 1 further comprising:

the infra-red sensor for generating signals corresponding to an amount of infra-red energy sensed passing through the lens.

7. The improvement of claim 6 further comprising:

a program stored in memory for processing the signals from the infra-red sensor; and a central processing unit for executing the program to process the data in accordance with the program.

8. The improvement of claim 7 further comprising:

the central processing unit for generating output signals corresponding to the processed data in accordance with the program; and an output device for receiving the output signals and for converting the output signals into perceivable form.

9. The improvement of claim 7 wherein the program further comprises:

means for storing data in retrievable form, wherein at least a portion of the data corresponds to an amount of infra-red energy sensed passing through the lens; and means for converting at least the portion of the stored data corresponding to an amount of infra-red energy into corresponding temperature values.

10. The improvement of claim 9 wherein the program further comprises:

means for processing the stored data to generate an output signal corresponding to a torque of the material.

11. A method for measuring a torque of a material to be tested in a viscometer having a rotatable member and a substantially stationary wall engageable with material to be measured, comprising the steps of:

rotating the rotatable member, and shearing material to be measured during undisturbed laminar flow across a face of a lens extendible through at least a portion of the wall of the viscometer; and sensing infra-red energy with an infra-red sensor alignable through the lens for directly measuring infra-red energy created while the material shears across the face of the lens in response to the rotatable member moving with respect to the lens and substantially stationary wall.

12. The method of claim 11 further comprising the step of:

forming the lens with a smooth seamless edge between the face of the lens and the surface of the wall, the material shearing along the surface of the wall and across the face of the lens undisturbed by the smooth seamless edge.

13. The method of claim 11 further comprising the step of:

positioning the sensor spaced from the wall.

14. The method of claim 11 further comprising the step of:

forming the lens from an optically transparent material.

15. The method of claim 11 further comprising the step of:

coating the lens with boron applied to the face engageable with the material to be measured.

16. The method of claim 11 further comprising the step of:

generating signals corresponding to an amount of infra-red energy sensed passing through the lens with the infra-red sensor.

17. The method of claim 16 further comprising the steps of:

processing the signals from the infra-red sensor in accordance with a program stored in memory; and executing the program with a central processing unit to process the data in accordance with the program.

18. The method of claim 17 further comprising the steps of:

generating output signals with the central processing unit corresponding to the processed data in accordance with the program;

receiving the output signals with an output device; and converting the output signals into perceivable form with the output device.

19. The method of claim 17 further comprising the steps of:

storing data in retrievable form, wherein at least a portion of the data corresponds to an amount of infra-red energy sensed passing through the lens; and converting at least the portion of the stored data corresponding to an amount of infra-red energy into corresponding temperature values.

20. The method of claim 19 further comprising the step of:

processing the stored data to generate an output signal corresponding to a torque of the material.

* * * * *